United States Patent [19]

Mosley

[11] Patent Number: 5,628,432
[45] Date of Patent: May 13, 1997

[54] PERSONAL COOLING SYSTEM

[76] Inventor: Julius Mosley, 2200 17th Ave. South, St. Petersburg, Fla. 33712

[21] Appl. No.: 627,086

[22] Filed: Apr. 3, 1996

[51] Int. Cl.⁶ .................................................. B65D 83/14
[52] U.S. Cl. ................ 222/175; 222/189.1; 222/394; 222/402.1; 239/397.5; 239/337
[58] Field of Search .................... 222/175, 146.6, 222/402.1, 189.1, 394; 239/152, 337, 397.5

[56] References Cited

U.S. PATENT DOCUMENTS

| | | | |
|---|---|---|---|
| 577,362 | 2/1897 | Ettlinger | 239/602 |
| 2,774,628 | 12/1956 | Engstrum | 222/189.1 |
| 3,209,954 | 10/1965 | Webster | 222/189.1 |
| 3,383,879 | 5/1968 | Tice | 222/402.13 X |
| 3,445,046 | 5/1969 | Wilson | 222/175 X |
| 3,913,842 | 10/1975 | Singer | 239/337 |
| 4,142,652 | 3/1979 | Platt | 222/189.1 X |
| 4,162,764 | 7/1979 | Millsap | 239/152 |
| 4,305,925 | 12/1981 | Vogel | 222/402.1 X |
| 4,580,690 | 4/1986 | Mulawski | 220/89.2 |
| 4,936,487 | 6/1990 | Mader et al. | 222/402.13 X |
| 4,951,857 | 8/1990 | Carr | 224/230 |
| 5,180,109 | 1/1993 | Schwartzbauer et al. | 239/346 |
| 5,232,137 | 8/1993 | Devine | 222/175 X |
| 5,348,190 | 9/1994 | Mizzi et al. | 222/402.1 X |
| 5,477,993 | 12/1995 | Maeda | 222/402.13 |

*Primary Examiner*—Kevin P. Shaver

[57] ABSTRACT

The present invention relates to a system which enables a person to cool a particular portion of their body. The cooling is achieved through the use of a canister of compressed air which is dispensed over the portions of the user's body to be cooled. Portability of the canister is afforded through the use of a resilient belt clip. Furthermore, a directional cone is secured adjacent the dispensing end to enable a more accurate placement of the cooling air.

9 Claims, 3 Drawing Sheets

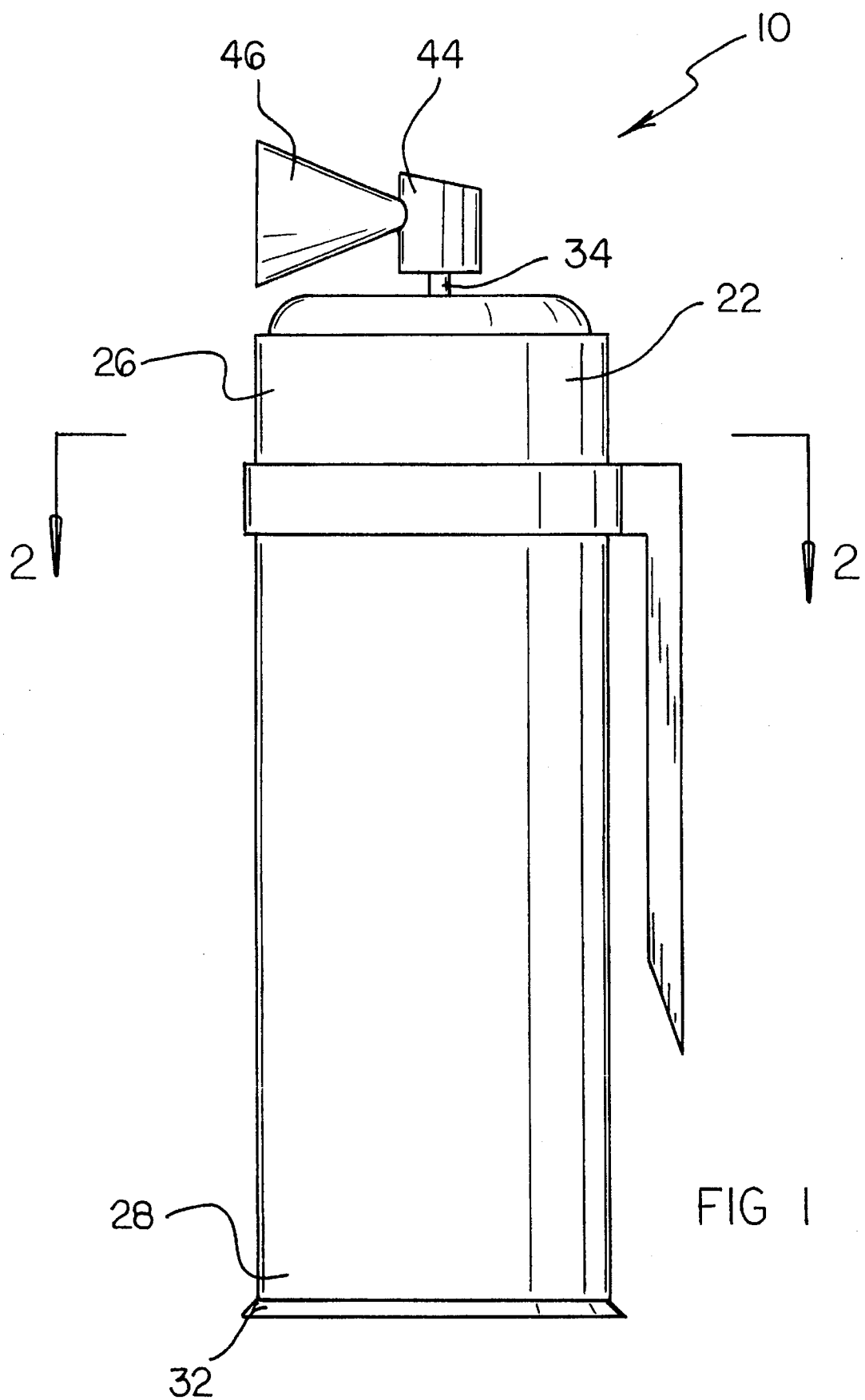

PERSONAL COOLING SYSTEM

BACKGROUND OF THE INVENTION

1. Field of the Invention

The present invention relates to personal cooling system and more particularly pertains to canister of air which facilitates the cooling of various body parts.

2. Description of the Prior Art

The use of aerosol containers is known in the prior art. More specifically, aerosol containers heretofore devised and utilized for the purpose of dispensing a gas are known to consist basically of familiar, expected, and obvious structural configurations, notwithstanding the myriad of designs encompassed by the crowded prior art which has been developed for the fulfillment of countless objectives and requirements.

The following U.S. Patents are provided as illustrative the prior art associated with the present invention. U.S. Pat. No. 5,348,190 to Mizzi et al discloses a insert module for an aerosol container. U.S. Pat. No. 5,232,137 to Devine discloses an apparatus for carrying a spray can. U.S. Pat. No. 5,180,109 to Schwartzbauer et al. discloses a single use spray dispensing assembly. U.S. Pat. No. 4,951,857 to Carr discloses a paint brush carrier. U.S. Pat. No. 4,580,690 to Mulawski discloses a coinless pressure relief device. U.S. Pat. No. 3,913,842 to Singer discloses a spray head for an aerosol can. Lastly, U.S. Pat No. 577,362 to Ettlinger discloses a hose nozzle.

In this respect, the personal cooling System according to the present invention substantially departs from the conventional concepts and designs of the prior art, and in doing so provides an apparatus primarily developed for the purpose of cooling various parts of the user's body. More specifically, none of the prior art illustrates a canister of compressed air utilized for the purpose of cooling various parts of the body. Additionally, none of the prior art illustrates the use of an insulting cone which is employed in delivering cold air to specific points upon the body of a user.

Therefore, it can be appreciated that there exists a continuing need for new and improved personal cooling system which can be used for cooling various parts of the user's body. In this regard, the present invention substantially fulfills this need.

SUMMARY OF THE INVENTION

In view of the foregoing disadvantages inherent in the known types of aerosol containers now present in the prior art, the present invention provides an improved personal cooling system. As such, the general purpose of the present invention, which will be described subsequently in greater detail, is to provide a new and improved personal cooling system and method which has all the advantages of the prior art and none of the disadvantages.

To attain this, the present invention essentially comprises a system which employs a metallic thin walled cylindrical canister having a diameter, an interior, an upper end, a lower end and an intermediate exterior surface therebetween. A lower base is coupled to the lower end of -the canister and has a diameter larger than the diameter of the canister. The metallic thin wall effects heat transfer from the interior to the exterior of the canister. A stem is secured to the upper end of the canister and serves to interconnect the interior and exterior of the canister. A button is included which has an upper surface, a forward portion, a rearward portion and a cylindrical surface interconnecting the forward and rearward portions, a lower end with opening therein, an opening formed within the forward portion, and a passage interconnecting the opening of the lower end and the opening of the forward portion. The upper surface of the button slopes from the forward toward the rearward portion. The system utilizes a directional cone having a proximal end and a distal end, wherein the proximal end is interconnected to the opening formed within the forward portion. A resilient belt clip is employed which is defined by two semicircular canister engaging portions and a belt securing portion interconnecting the two canister engaging portions. The two semicircular engaging portions together defining a diameter. The belt securing portion is intermediate of and perpendicular to the two semicircular canister engaging portions. This belt clip is constructed from a resilient thermoplastic material which affords a degree of flexibility. The diameter of the two engaging portions is substantially the same diameter as the canister and is deformable to a diameter substantially larger than the diameter of the canister.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent of legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide new and improved personal cooling system which have all the advantages of the prior art aerosol containers and none of the disadvantages.

It is another object of the present invention to provide new and improved personal cooling System which may be easily and efficiently manufactured and marketed.

It is further object of the present invention to provide new and improved personal cooling system which are of durable and reliable constructions.

An even further object of the present invention is to provide new and improved personal cooling system which are susceptible of a low cost of manufacture with regard to both materials and labor, and which accordingly are then susceptible of low prices of sale to the consuming public, thereby making such personal cooling system economically available to the buying public.

Still yet another object of the present invention is to provide new and improved personal cooling system which provide in the apparatuses and methods of the prior art some of the advantages thereof, while simultaneously overcoming some of the disadvantages normally associated therewith.

Even still another object of the present invention is to enable the cooling of various body parts through the use of a portable canister of compressed air.

Lastly, it is an object of the present invention to provide new and improved system which enables a person to cool a particular portion of their body. The cooling is achieved through the use of a canister of compressed air which is dispensed over the portions of the user's body to be cooled. Portability of the canister is afforded through the use of a resilient belt clip. Furthermore, a directional cone is secured adjacent the dispensing end to enable a more accurate placement of the cooling air.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is an elevational view of the preferred embodiment of the personal cooling system constructed in accordance with the principles of the present invention.

DESCRIPTION OF THE PREFERRED EMBODIMENT

Figure 3:
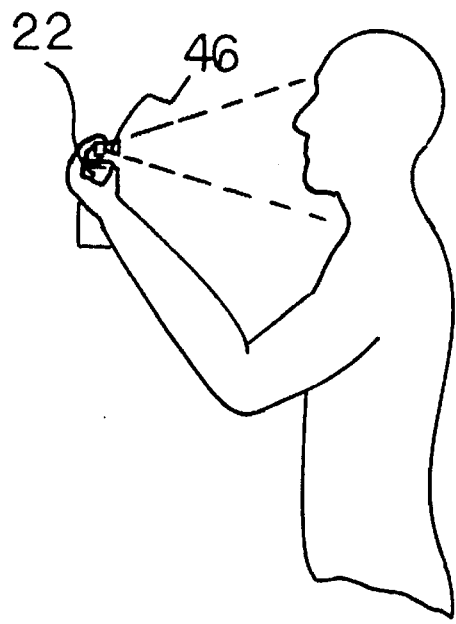
FIG. 3 is a view of a user employing the device of the present invention.
Figure 2:
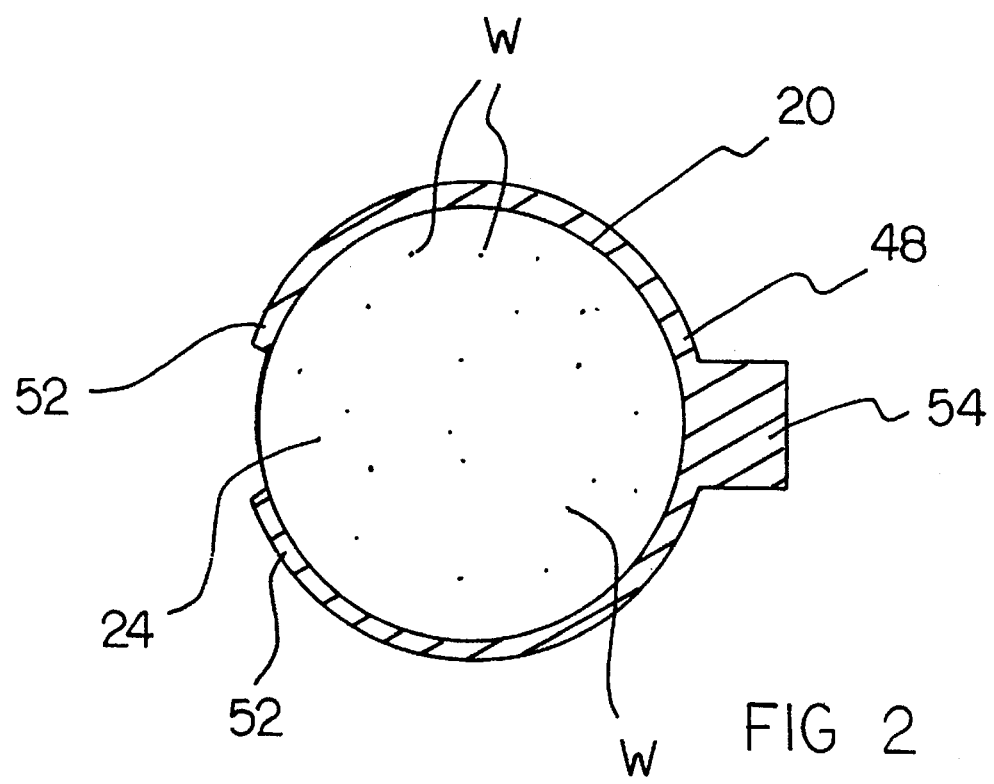
FIG. 2 is a view taken along line 2—2 of FIG. 1.
Figure 4:
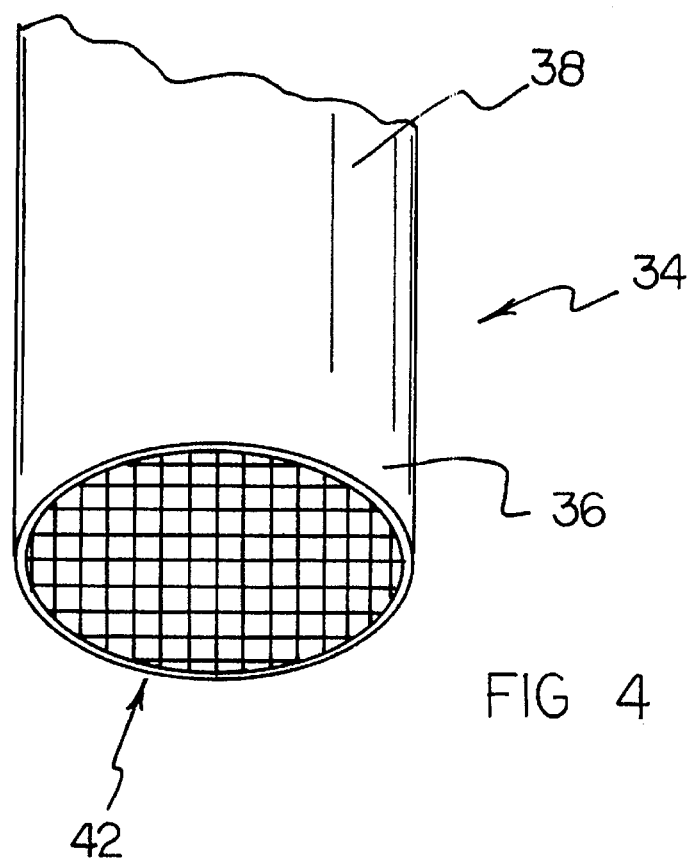
FIG. 4 is a view of the filter employed with the present invention.
Figure 5:
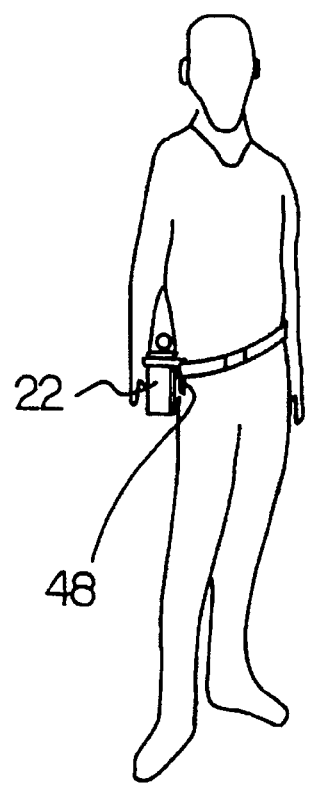
FIG. 5 is a view of the present invention clipped onto a user's belt.

With reference now to the drawings, and in particular to FIG. 1 thereof, the preferred embodiment of the new and improved personal cooling system embodying the principles and concepts of the present invention and generally designated by the reference numeral 10 will be described.

The present invention relates to a system which enables a person to cool a particular portion of their body with a directed flow of air. This cooling is achieved through the use of a canister of compressed air which is dispensed over the portions of a user's body. Portability of the canister is afforded through the use of a resilient belt clip. Furthermore, a directional cone is secured adjacent the dispensing end of the canister to enable a more accurate placement of the cooling air. The various components of the present invention, as well as the manner in which they interrelate, will be described in greater detail hereinafter.

The canister 22 of the present invention is constructed from a thin wall 20 of a metallic material. Additionally, this cylindrical canister 22 is defined, in part, by the following elements: a diameter; an interior 24; an upper end 26; a lower end 28; and an intermediate exterior surface therebetween. A lower base 32 is coupled to the lower end 28 of the canister 22. This base 32 has a diameter which is larger than the diameter of the canister 22 to provide stability to the canister 22 when standing vertically. In the preferred embodiment, the base 32 is constructed from a non-metallic, non heat transferring material, such as rubber. The metallic thin wall 20 of the canister 22 effects heat transfer from the interior 24 to the exterior of the canister 22. The degree of heat transfer is determined by two factors: the specific material of the canister 22; and the thickness of canister wall 20. The canister 22 of the present invention maximizes both of these factors, providing a canister 22 of a thin walled metallic material.

The dispensing mechanism associated with the present invention will next be described. A stem 34, having a lower end 36 and an upper end 38, is secured within the upper end 22 of the canister 22 and serves to interconnect the interior 24 and exterior of the canister 22. A button 44 is employed in permitting the egress of compressed air through the stem 34 of the dispensing mechanism. This button 44 is secured to the upper end 38 of the stem 34. The button 44 is defined, in part, by the following elements: an upper surface; a forward portion; a rearward portion; and a cylindrical surface interconnecting the forward and rearward portions. This button 44 further includes a lower end with opening therein, and an opening formed within the forward portion. A passage serves to interconnect the opening of the lower end and the opening of the forward portion. As is illustrated in FIG. 1, the upper surface of the button 44 is sloped from the forward toward the rearward portion. This sloping provides for increased surface area upon which a user may depress the button 44.

In order to achieve precise directional spraying of the cooling air associated with the present invention a directional cone 46 is employed. This directional cone 46 is defined by a proximal end and a distal end. The proximal end is interconnected to the opening formed within the forward portion. The button 44 of the dispensing mechanism is rotatably interconnected with the stem 34, thus permitting the directional cone 46 to be revolved about the longitudinal axis of the stem 34. In the preferred embodiment, the cone 46 is constructed from a plastic material. The directional cone 46 also aids in keeping the dispensed air cool. This feature of the cone 46 will be described in greater detail hereinafter.

The belt clip 48 of the present invention provides a means by which the system of the present invention can be transported. The resilient belt clip 48 has two semicircular canister engaging portions 52 and a belt securing portion 54 interconnecting the two canister engaging portions 52. The two semicircular engaging portions 52 together define a diameter. The belt securing portion 54 is intermediate of, and perpendicular to, the two semicircular canister engaging portions 52. The belt clip 48 is constructed from a resilient thermoplastic or plastic material which affords it a degree of flexibility. In a relaxed orientation, the diameter of the two engaging portions 52 is substantially the same as the diameter of the canister 22. However, the two engaging portions 52 can be deformable to a diameter substantially larger than the canister diameter. This deformability enables the engaging portions 52 to be positioned around the diameter of the canister 22.

In the preferred embodiment, the canister 22 is filled with pure air under compression. Thus, the gas under compression consists essentially of Nitrogen and Oxygen. It is an important aspect of the present invention that the air not be contaminated with any chemicals, preservatives or other toxic substances. To achieve this, a filter 42 is utilized within the interior 24 of the canister 22 adjacent the dispensing mechanism. Specifically, the filter 42 is positioned within the lower end 36 of the stem 34. This filter 42 has openings small enough to remove any harmful particles of dust from the air stream which are unfit for human consumption. Furthermore, the filter 42 is constructed from a material which absorbs any unwanted chemicals which are unfit for human consumption. Thus, the filter 42, along with employing only purified, or otherwise filtered, air in the canister 22, ensures that air which exits the directional cone 46 is fit for human consumption.

The compression of the air ensures its egress from the canister 22 when the button 44 of the dispensing mechanism is depressed. However, the compression also effects the contents of the canister 22 in two other ways. First, when the air is released from the canister 22, thereby becoming uncompressed, a cooling of the air is effected. In this manner any air released from the canister 22 is thereby cooled sufficiently to give the user a desired result. Second, as compressed air is being discharged, a cooling of the air remaining within the canister 22 is achieved. Thus, the hand of the user gets cooled by thermal contact through the thin canister wall 20. Both of these effects are governed by the equation:

$$PV=RT$$

wherein P is the pressure of the gas, V is the molar volume of the gas, R is the gas constant of the gas, and T is the absolute temperature of the gas. Additionally, the directional cone 46 associated with the dispensing mechanism prohibits the cooled air initially exiting from the canister 22 from comingling with the warmer ambient air. Additionally, the directional cone 46 is constructed from plastic, to partially insulate the cooled air from the warmer ambient air, thereby preventing the thermal contact between the exiting air and ambient air. Thus, the directional cone 46 also serves as an insulting cone. Through the use of the insulting cone 46, the cooled air is delivered to a portion of the body while still cold.

In an alternate embodiment of the invention, there is provided within the canister 22 a small quantity of purified water W. By way of example, in a canister adapted to maintain about one pint of compressed air, there would be added an additional quantity of purified water in the nature of one to two tablespoons. This would constitute between about 2.5 and 5.0 percent by volume of the contents of the canister. Larger canisters or smaller canisters could be utilized so long as such percentage relationship continues. Once such is utilized, a user would shake the canister prior to dispensing its contents. The water would be scattered around, partially suspended, misted and vaporized within the canister so that upon depressing the button and releasing a portion of the condensed air with its cooling effect, a small quantity of misted water vapor would be entrained within the flow of compressed air from the canister and through the nozzle. More or less water would be provided within the canister as a function of the extent of the moister to be dispensed.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A portable belt worn personal cooling system comprising in combination:

a metallic thin walled cylindrical canister having a diameter, an interior, an upper end, a lower end and an intermediate exterior surface therebetween, a lower base coupled to the lower end of the canister and having a diameter larger than the diameter of the canister, the metallic thin wall effecting heat transfer from the interior to the exterior of the canister;

a compressed gas consisting essentially of Nitrogen and Oxygen positioned within the interior of the canister;

a stem having a lower and upper end, the stem secured within the upper end of the canister and interconnected to the interior of the canister, a filter positioned within the lower end of the stem, the filter having openings which remove particles unfit for human consumption, and the filter being constructed from a material which absorbs any chemicals unfit for human consumption;

button having an upper surface, a forward portion, a rearward portion and a cylindrical surface interconnecting the forward and rearward portions, a lower end with opening therein, an opening formed within the forward portion, a passage interconnecting the opening of the lower end and the opening of the forward portion, the upper surface sloping from the forward toward the rearward portion;

a plastic insulating cone having a proximal end and a distal end, the proximal end interconnected to the opening formed within the forward portion, the insulating cone functioning to prevent thermal contact between the air exiting the canister and the ambient air a resilient plastic belt clip having two semicircular canister engaging portions and a belt securing portion interconnecting the two canister engaging portions, the two semicircular engaging portions together defining a diameter, the belt securing portion being intermediate of and perpendicular to the two semicircular canister engaging portions, the belt clip constructed from a resilient thermoplastic material which affords a degree of flexibility, the diameter of the two engaging portions being substantially the same diameter as the canister and being deformable to a diameter substantially larger than the diameter of the canister.

2. A portable belt worn personal cooling system comprising in combination:

a cylindrical canister having a diameter, an interior, an upper end, a lower end and an intermediate exterior surface therebetween;

a stem secured within the upper end of the canister and interconnected to the interior of the canister;

button having an upper surface, a forward portion, a rearward portion and a cylindrical surface interconnecting the forward and rearward portions, a lower end with opening therein, an opening formed within the forward portion, a passage interconnecting the opening of the lower end and the opening of the forward portion;

a plastic insulating cone having a proximal end and a distal end, the proximal end interconnected to the opening formed within the forward portion, the insulating cone functioning to prevent thermal contact between the air exiting the canister and the ambient air.

3. The system as described in claim 2, wherein:

the canister is constructed from a metallic material and is constructed with a thin wall which enables heat transfer from the interior to the exterior of the canister.

4. The system as described in claim 2 further comprising:

a resilient belt clip having two semicircular canister engaging portions and a belt securing portion interconnecting the two canister engaging portions, the two semicircular engaging portions together defining a diameter, the belt securing portion being intermediate of and perpendicular to the two semicircular canister engaging portions, the belt clip constructed from a resilient thermoplastic material which affords a degree of flexibility, the diameter of the two engaging portions is substantially the same diameter as the canister and is deformable to a diameter substantially larger than the diameter of the canister.

5. The system as described in claim 2, further comprising:

a filter positioned within the lower end of the stem, the filter having openings which remove particles unfit for human consumption, and the filter being constructed from a material which absorbs any chemicals unfit for human consumption.

6. The system as described in claim 2, further comprising:

a compressed gas consisting essentially of Nitrogen and Oxygen positioned within the interior of the canister.

7. The apparatus as set forth in claim 2, and further including a quantity of water within the canister.

8. The apparatus as set forth in claim 7 wherein the water consists of between about 2.5 percent and 5.0 percent by volume of the contents of the canister.

9. The apparatus as set forth in claim 2 wherein the length of the cone is less than the radius of the canister.

* * * * *